(12) United States Patent
Trinidad

(10) Patent No.: US 7,972,351 B2
(45) Date of Patent: Jul. 5, 2011

(54) BALLOON FOLDING DESIGN AND METHOD AND APPARATUS FOR MAKING BALLOONS

(75) Inventor: Jeffrey S. Trinidad, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1293 days.

(21) Appl. No.: 10/896,522

(22) Filed: Jul. 13, 2004

(65) Prior Publication Data

US 2006/0015134 A1    Jan. 19, 2006

(51) Int. Cl.
*A61M 29/00* (2006.01)
(52) U.S. Cl. .............. 606/194; 606/167; 604/103.07
(58) Field of Classification Search .......... 606/191, 606/194, 198, 159, 167, 170; 604/103.08, 604/103.04, 96.01, 102.01, 103.11, 103.13–103.14, 604/103.06–103.07, 104
See application file for complete search history.

(56) References Cited

U.S. PATENT DOCUMENTS

| | | | |
|---|---|---|---|
| 4,490,421 A | 12/1984 | Levy | 428/35 |
| 4,758,223 A * | 7/1988 | Rydell | 604/97.02 |
| 5,037,392 A | 8/1991 | Jillstead | 604/96 |
| 5,053,007 A | 10/1991 | Euteneuer | 604/96 |
| 5,087,246 A | 2/1992 | Smith | 604/96 |
| 5,147,302 A | 9/1992 | Euteneuer et al. | 604/103 |
| 5,163,989 A * | 11/1992 | Campbell et al. | 65/110 |
| 5,196,024 A | 3/1993 | Barath | 606/159 |
| 5,209,799 A | 5/1993 | Vigil | 156/156 |
| 5,226,887 A | 7/1993 | Farr et al. | 604/96 |
| 5,318,587 A | 6/1994 | Davey | 606/194 |
| 5,320,634 A * | 6/1994 | Vigil et al. | 606/159 |
| 5,342,307 A | 8/1994 | Euteneuer et al. | 604/103 |
| 5,350,361 A | 9/1994 | Tsukashima et al. | 604/96 |
| 5,456,666 A | 10/1995 | Campbell et al. | 604/96 |
| 5,458,572 A | 10/1995 | Campbell et al. | 604/96 |
| 5,478,319 A | 12/1995 | Campbell et al. | 604/96 |
| 5,549,552 A | 8/1996 | Peters et al. | 604/96 |
| 5,718,684 A | 2/1998 | Gupta | 604/96 |
| 5,746,745 A | 5/1998 | Abele et al. | 606/108 |
| 5,797,935 A | 8/1998 | Barath | 609/159 |
| 5,882,334 A | 3/1999 | Sepetka et al. | 604/96 |
| 6,013,055 A | 1/2000 | Bampos et al. | 604/96 |
| 6,033,380 A | 3/2000 | Butarie et al. | 604/96 |
| 6,071,285 A | 6/2000 | Lashinski et al. | 606/108 |
| 6,126,652 A | 10/2000 | McLeod et al. | 606/1 |
| 6,135,982 A | 10/2000 | Campbell | 604/96.01 |
| 6,146,356 A | 11/2000 | Wang et al. | 604/96 |
| 6,171,278 B1 | 1/2001 | Wang et al. | 604/96 |
| 6,258,099 B1 * | 7/2001 | Mareiro et al. | 606/108 |
| 6,428,568 B2 * | 8/2002 | Gaudoin et al. | 623/1.11 |
| 6,491,711 B1 * | 12/2002 | Durcan | 606/194 |
| 6,544,224 B1 * | 4/2003 | Steese-Bradley | 604/103.06 |
| 2002/0163104 A1 | 11/2002 | Motsenbocker et al. | 264/320 |

(Continued)

FOREIGN PATENT DOCUMENTS

| | | |
|---|---|---|
| EP | 0565796 | 10/1993 |
| WO | WO 9423787 | 10/1994 |

*Primary Examiner* — Theodore J Stigell
(74) *Attorney, Agent, or Firm* — Vidas, Arrett & Steinkraus, P.A.

(57) ABSTRACT

An expandable balloon for a medical device having a static state, at least one first expanded state, and at least one second expanded state, the expandable balloon having a substantially polygonal geometric shape in the static state.

16 Claims, 6 Drawing Sheets

U.S. PATENT DOCUMENTS

| | | |
|---|---|---|
| 2003/0083687 A1 | 5/2003 | Pallazza ............................ 606/91 |
| 2003/0163148 A1* | 8/2003 | Wang et al. .................... 606/159 |
| 2003/0163157 A1 | 8/2003 | McMorrow et al. ........... 606/194 |
| 2004/0073165 A1 | 4/2004 | Musbach et al. .......... 604/103.07 |
| 2005/0038383 A1* | 2/2005 | Kelley et al. .............. 604/103.06 |
| 2005/0149102 A1* | 7/2005 | Radisch et al. ................ 606/194 |

\* cited by examiner

BALLOON FOLDING DESIGN AND METHOD AND APPARATUS FOR MAKING BALLOONS

BACKGROUND OF THE INVENTION

Atherosclerotic cardiovascular disease is common, and is caused by a narrowing of the arterial lining due to atherosclerotic plaques. Medical balloons are used in the body in the treatment of atherosclerotic cardiovascular disease and include dilatation devices for compressing plaque and for expanding prosthetic devices such as stents at a desired location in a bodily vessel.

Percutaneous transluminal coronary angioplasty, or balloon angioplasty, is a non-invasive, non-surgical means of treating peripheral and coronary arteries. This technique consists of inserting an uninflated balloon catheter into the affected artery. Dilation of the diseased segment of artery is accomplished by inflating the balloon which pushes the atherosclerotic lesion outward, thereby enlarging the arterial diameter.

Another type of medical balloons are those having cutting edges, also referred to as atherotomes or blades, for recanalizing and dilating a diseased vessel, and facilitating balloon angioplasty procedures.

In either type of application, it is typically necessary for the balloon to traverse a tortuous anatomy as it is being delivered to the location in a bodily vessel; it is desirable for the balloon to assume as low a profile, i.e. the outer diameter of the distal end portion of the balloon, as possible. Considerable effort has been put forth in the development of dilatation balloons with a low profile by minimizing the dimensions of the core or the inner tube which extends through the balloon to its distal end, and by reducing the wall thickness of the balloon itself.

One way to achieve a low profile in the deflated state of the balloon is by folding the balloon to form a number of wings. In the deflated state, the balloon collapses upon itself forming flaps or wings that must be folded or wrapped around the balloon catheter to allow it to be withdrawn from the patient's vasculature after use.

Also prior to use, the balloon is typically folded or wrapped about the balloon catheter to fit within and pass through the guide catheter lumen. When inflation fluid is applied to the deflated balloon, the balloon wings or flaps unwrap and the balloon inflates to a fully expanded condition.

Various techniques or balloon constructions have been employed to facilitate the folding of the balloon about the balloon catheter in a uniform manner upon evacuation and deflation of the balloon after use.

One approach has been to construct the balloon of a cylinder of material, such as polyethylene, that is uniform about its circumference but can be heat set after it is wrapped or folded to form curved, overlapping flaps or wings extending from fold lines in a manner described further below. Heat setting of the balloon results in a balloon that when, upon application of negative pressure during deflation, will return fairly closely to its tightly wrapped heat set configuration.

Another approach has been taken to fabricate the balloon itself with fold line structures and flap shapes, particularly for use with balloons formed of stronger polyesters, for example, polyethylene terepthalate (PET).

There remains a need, however, for innovative and improved methods for folding balloons and for improved balloon refold.

All US patents and applications and all other published documents mentioned anywhere in this application are incorporated herein by reference in their entirety.

Without limiting the scope of the invention a brief summary of the claimed embodiments of the invention is set forth below. Additional details of the summarized embodiments of the invention and/or additional embodiments of the invention may be found in the Detailed Description of the Invention below.

SUMMARY OF THE INVENTION

The present invention relates to expandable balloons for catheters for insertion into parts of the body and particularly to a catheter with a balloon that after expansion, use and evacuation of inflation fluids will fold itself into a predetermined shape of limited diameter so that it can be easily withdrawn from the body.

While the present invention finds utility for balloons used for coronary angioplasty procedures, the present invention also finds utility for other types of medical balloons including, but not limited to, cutting balloons, balloons used in the biliary duct, urinary tract, expandable balloons for medical delivery devices including stents, etc.

The balloons according to the present invention have at least one static state, at least one expanded state, and at least one deflated state, and can be formed such that they have a substantially polygonal geometric shape in at least the static state which facilitates refolding of the balloon after evacuation and deflation. The expandable balloon according to the invention can be formed such that they may also exhibit a substantially polygonal geometric structure in the at least one expanded state which may be similar to or different than the substantially polygonal geometric structure in the static state.

The balloons suitably have two or more wings, even more desirably three or more wings, and most desirably four or more wings. The wings may be desirably disposed uniformly about a reference circle. Each wing may also have a substantially polygonal geometric shape.

In some embodiments, the balloons have a plurality of wings such that they form a star-like structure. As used herein, the term "star" shall be used to refer to any structure having a plurality of wings wherein a plurality is 3 or more wings. In some embodiments, the balloons have four wings forming a four-point star-like structure.

The geometric structure of the balloons described herein facilitates refolding of the balloon after evacuation and deflation.

Other benefits and advantages will become apparent from the following description.

All patents discussed herein are incorporated by reference herein in their entirety.

DETAILED DESCRIPTION OF THE INVENTION

Figure 1:
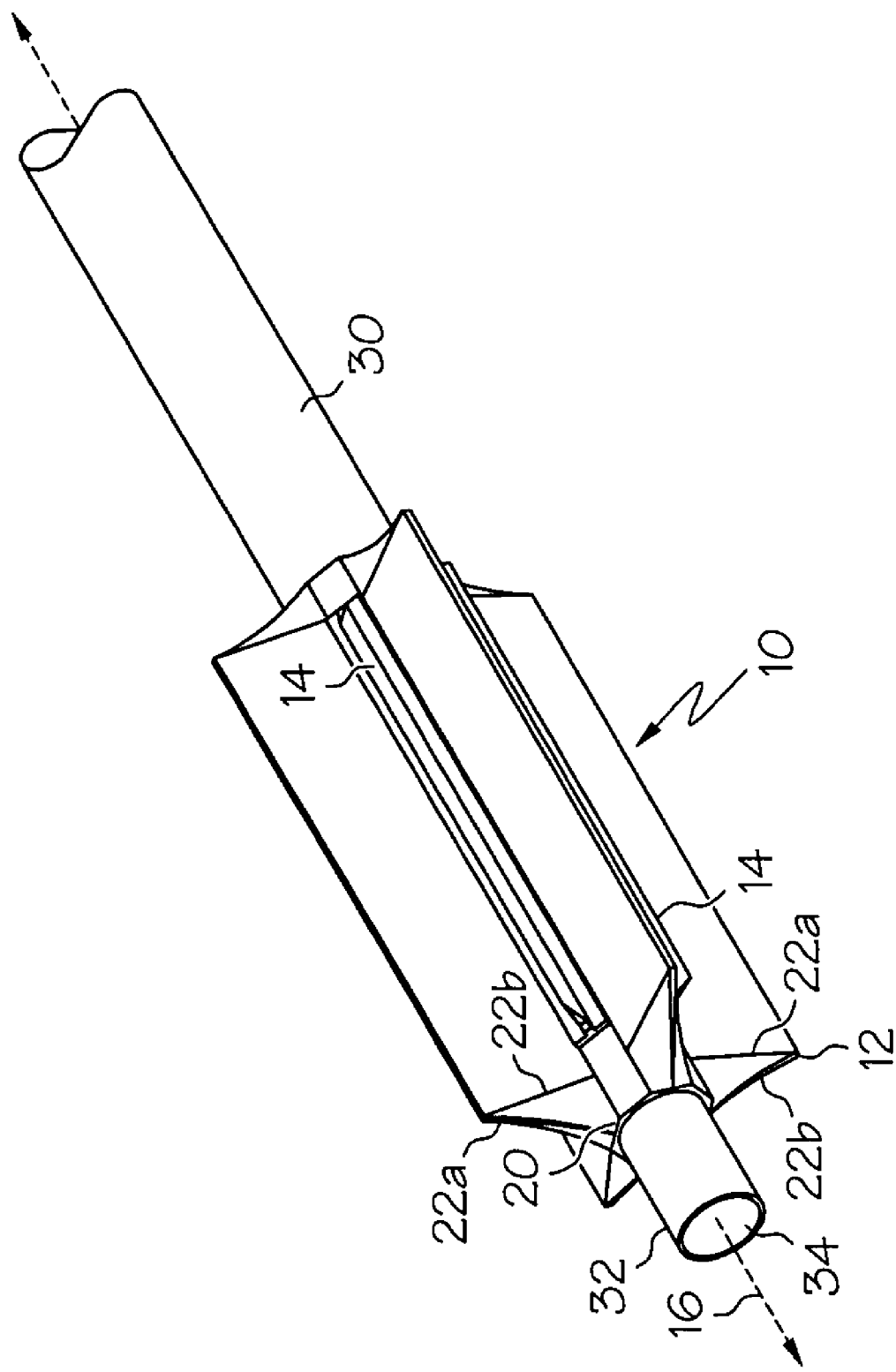
FIG. 1 is an enlarged perspective view of a cutting catheter balloon in accordance with one embodiment of the invention, shown in a deflated state.

While this invention may be embodied in many different forms, there are described in detail herein specific embodiments of the invention. The present disclosure is an exemplification of the principles of the invention and is not intended to limit the invention to the particular embodiments illustrated.

For the purposes of this disclosure, like reference numerals in the figures shall refer to like features unless otherwise indicated.

While the expandable balloons described herein may take on many geometric configurations, there will be described herein, some specific embodiments of the invention.

The expandable balloons according to the invention are expandable from a folded condition for insertion into the body to an expanded condition with a diameter in the expanded state being substantially greater than the folded condition to provide medical treatment and, after treatment, being revertible into a folded condition of predetermined configuration.

The balloons according to the invention have a static state, at least one first expanded state, and at least one deflated state. In some embodiments, the balloons have at least one second expanded state. Balloons are typically deflated from their static state prior to wrapping or folding by applying negative pressure. The balloons according to the invention have substantially polygonal geometric shapes which facilitate refolding of the dilation balloon after evacuation and deflation. As defined herein, a substantially polygonal geometric shape shall refer to those having three or more sides. In some embodiments described herein, the substantially polygonal geometric shape is one having five or more sides.

The balloons may also have a substantially polygonal geometric shape in the at least one first expanded state, in the at least one second expanded state, or both. The substantially polygonal geometric shape in the at least one first expanded state may be the same as or different than the substantially polygonal geometric shape of the balloon in the at least one second expanded state. Thus, the balloons according to the invention may have more than one expanded state, and in each expanded state, exhibit a substantially polygonal geometric shape.

"Substantially polygonal" shall be used herein to refer to the structures having three or more sides, of which the side forming the base of the polygon may have a slight curvature as defined by the balloon structure. The base line may also be substantially straight depending on the balloon structure. The base line shall be defined as that line tangential to the guide wire lumen.

As used herein, the term "static state" refers to a medical balloon as it is removed from the mold, prior to deflation, or expansion.

The term "fully expanded" shall refer to the maximum amount of expansion that the medical balloon will undergo during use and in some cases, will correspond with the at least one second expanded state.

The term "deflated" may refer to a medical balloon which has been evacuated or deflated from its static state. Of course, a balloon may also be deflated from a fully expanded state, but remains in a state of expansion, if it is between the static state and the fully expanded state. An intermediate expanded state in some instances may correspond to the at least one first expanded state.

Any suitable inflation pressures may be employed herein and depend on the type of balloon, as well as the application for which the balloon is employed. Inflation pressures used may be anywhere from about 8 to about 30 atmospheres, depending on the type of balloon material employed, the wall thickness, layers employed, and so forth. Balloons employed in the peripheral vessels, for example, may have rated burst pressures in the 12-14 atmosphere range pressure while balloons used in the coronary vessels may have rated burst pressures of about 18-21 atmospheres, for example. Of course these numbers are intended for illustrative purposes only, and not as a limit on the scope of the invention. Modifying the design of a balloon, such as with reinforcement, for example with braiding, may lead to higher rated burst pressures.

Balloons are typically formed by blowing and stretching of a segment of extruded polymer tubing referred to as a balloon "preform" or parison. The balloon preforms according to the invention may be substantially cylindrical or substantially square, for example. Furthermore, the inner and outer surface of the balloon preforms may have a different geometric shape.

Turning now to the figures, FIG. 1, shows an enlarged perspective view of a cutting balloon 10 disposed at the distal end of a catheter shaft 30 having an inflation lumen (not shown) extending therethrough. Catheter assemblies may be equipped with an inflation lumen running through a shaft upon which the balloon may be disposed. Fluid can be supplied through the inflation lumen to the balloon, and upon application of negative pressure to the inflation lumen, the balloon deflates. The balloon is shown in a deflated, but unwrapped or unfolded state. The balloon of FIG. 1 is shown having a four-point star structure.

Balloon 10 according to the invention may have a plurality of wings such as two, three, four, or more wings. In the embodiment illustrated in FIG. 1, balloon 10 is shown having a four-winged structure in a deflated state. Balloon 10 is shown having a longitudinal axis 16 represented by a dotted line. Each wing 12 may have a substantially polygonal geometric shape in a cross sectional view perpendicular to the longitudinal axis 16, the polygonal geometric shape having three or more sides. Each wing is formed having substantially straight sides connected by a base line 20 which is substantially straight or which has a slight curvature as determined by the shape of the balloon structure. In the embodiment shown in FIG. 1, each wing 12 is shown having a substantially triangular shape defined by two substantially straight lines 22a, 22b and a slightly curved base region 20. The base line shown in FIG. 1 is substantially shorter than the sides of each wing. Base region 20 is shown tangential to guide wire lumen 34 as defined by inner catheter shaft 32. In FIG. 1, balloon 10 is secured to inner catheter shaft 32 at the distal end and is secured to outer catheter shaft 30 at the proximal end.

The balloons according to the invention may further include atherotomes or blades. Located in between each wing 12 in this embodiment are atherotomes or blades 14. The term "atherotome" shall hereinafter be used to refer to any cutting edge on the balloon catheter device.

Balloon 10 may be formed from any suitable polymeric material including polyolefins such as polyethylene including low, medium and high density polyethylenes, and copolymers thereof, polyesters and copolymers thereof such as polyethylene terephthalate or polybutylene terephthalate; polyamides, i.e. nylon, and copolymers thereof such as polyether block amides, i.e. those sold under the tradename of PEBAX® from Atofina Chemicals in Philadelphia, Pa.; polyimides; and so forth.

Suitable balloon materials are described in commonly assigned U.S. Pat. Nos. 5,549,552, 5,882,334, 6,171,278 and 6,146,356, each of which is incorporated by reference herein in their entirety.

The balloons may be formed using conventional balloon forming techniques. Such processes are known in the art. One balloon forming technique is described in U.S. Pat. No. 4,490,421 to Levy which is incorporated by reference herein in its entirety. However, unlike other conventional processes, the balloon preform may be extruded into a substantially polygonal geometric shape, and the balloon may be formed in a mold having a substantially geometric polygonal shape. In one embodiment, the balloon preform is extruded into a shape which is substantially square and the tubing is then placed in a mold wherein the mold has a substantially polygonal shape which has a plurality of wings, each wing having a substantially polygonal geometric shape. It is important to note that the balloon preform has an inner and outer surface. Each of the inner surface and the outer surface may have the same geometric configuration, or in some embodiments, the inner and outer surface may have a different geometric shape. For example, the inner surface may define a square, while the outer surface has a circular geometric configuration.

Balloon 10 may be formed of any conventional dimensions and may be made in various sizes depending on the application, but balloons are typically from about 20 to about 30 mm in length, and from about 1.5 to about 8.0 mm in diameter.

Inner catheter shaft 32 may define a guide wire lumen 34 for accommodating a guide wire used to steer and manipulate balloon 10 within a patient's vasculature system during a medical procedure such as angioplasty.

Figure 2:
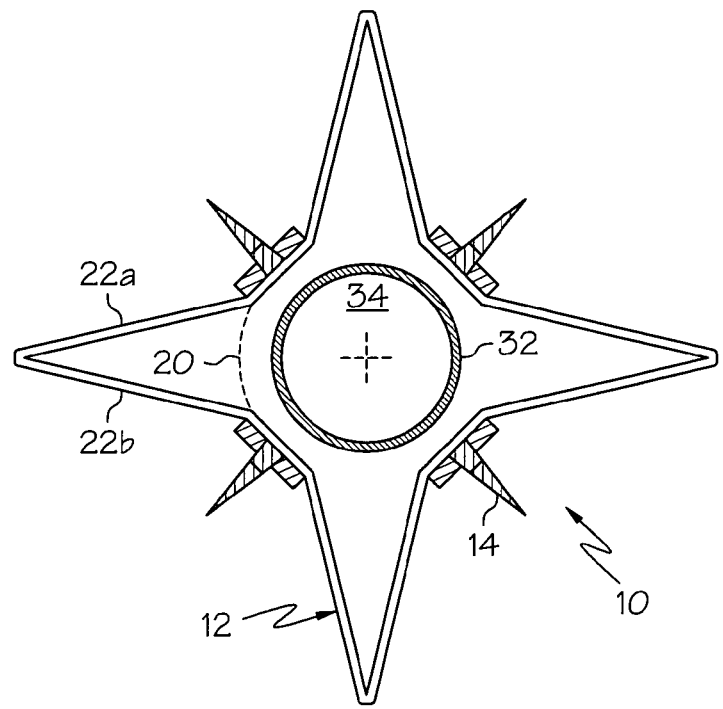
FIG. 2 is a cross-sectional view of a cutting catheter balloon substantially similar to that in FIG. 1 in a static state.

FIG. 2 illustrates generally at 10, a cross-sectional view perpendicular to the longitudinal axis of a balloon similar to that shown in FIG. 1, in a static state. As used herein, the term "static state" shall refer to the balloon state after being removed from the mold and prior to deflation or inflation. In this embodiment, balloon 10 is shown having a substantially polygonal geometric shape which is in the shape of a four-point star, the star having four wings 12, each wing having a substantially polygonal geometric shape, in particular a substantially triangular shape. Each side of the triangle, 22a, 22b, is connected by a base region 20 tangential to guide wire lumen 34 as defined by inner catheter shaft 32. In this embodiment, base region 20 has a slight curvature as represented by the dotted line 20. Between each of the wings 12, is shown atherotomes or blades 14.

Figure 3:
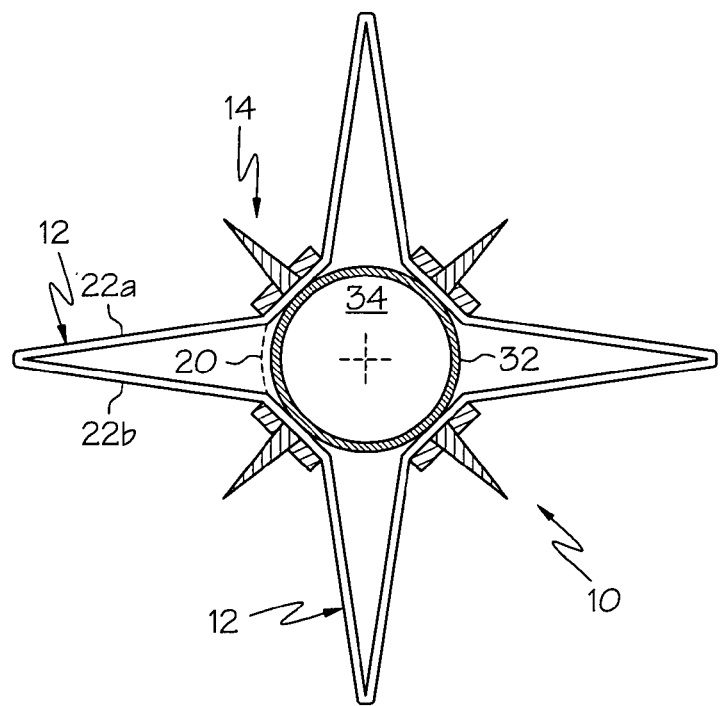
FIG. 3 is an expanded cross-sectional view of the cutting catheter balloon similar to that shown in FIG. 2 deflated from its static state during a balloon folding process.

FIG. 3 shows the same balloon as FIG. 2, but after having applied negative pressure, i.e. the balloon is deflated, such as during a balloon folding operation.

Any conventional balloon folding apparatuses and techniques may be employed in wrapping or folding of the balloons according to the invention.

Figure 4:
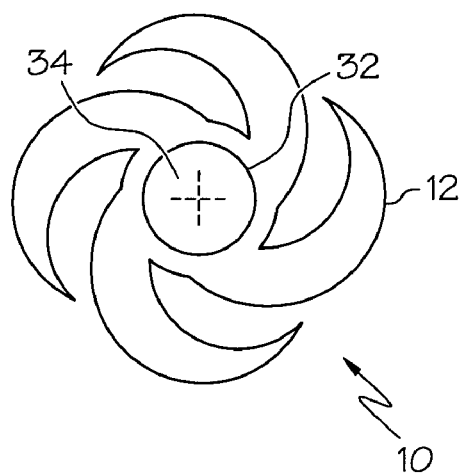
FIG. 4 is an enlarged cross-sectional end view of a catheter balloon with substantially similar geometric configuration to those shown in FIGS. 1-3 folded about the catheter shaft.

FIG. 4 is a cross-sectional depiction of a balloon 10 (not showing the blades) having a substantially similar configuration to those shown in FIGS. 1-3, with wings 12 folded about the inner catheter shaft 32.

For balloon folding or wrapping, current technologies typically employ a number of hard die-like structures which are moved radially inward toward the center of a partially expanded balloon. Negative pressure, i.e. a vacuum, is applied to the balloon during this balloon folding process. The balloon is typically placed in some sort of holding fixture, and then maintained in a partially expanded state until the dies have reached the end of their stroke. A vacuum is then applied to the balloon to deflate the balloon and form wings that conform to the configuration of the dies. The wings may then be wrapped or rolled around the circumference of the balloon.

Desirably, in the embodiment in which the balloon has a four-point star like structure, the blades of the folding apparatus may be circumferentially spaced at 90° intervals about the balloon.

Any suitable balloon folding apparatus may be employed herein. The above is only one exemplification of a balloon folding method and is not intended to limit the scope of the present invention. Balloon folding apparatuses and techniques are known in the art. For example, balloon folding apparatuses and methods thereof are discussed in commonly assigned copending U.S. Published application Nos. 2003/0083687A1 and 2003/0163157A1, both of which are incorporated by reference herein in their entirety.

Other balloon folding apparatuses and methods thereof are described in U.S. Pat. No. 5,350,361, U.S. Pat. No. 6,126,652, US 2002/0163104A1, U.S. Pat. No. 6,033,380, to mention only a few, each of which is incorporated by reference herein in its entirety. The present invention is not limited by the type of balloon folding apparatus or method used therein.

Once folded, the present invention typically does not require heat setting of the balloon, although this step does not have to be excluded and in some embodiments it may be desirable to employ a heat set.

Balloon protectors or sleeves may be employed to keep the balloon wrapped or folded prior to inflation and to help refold the balloon during and after deflation. If an elastic sleeve is provided, a guide wire may be passed along the balloon inside the sleeve. An example of this type of structure is described in U.S. Pat. No. 6,071,285, which is incorporated by reference herein in its entirety.

Figure 5:
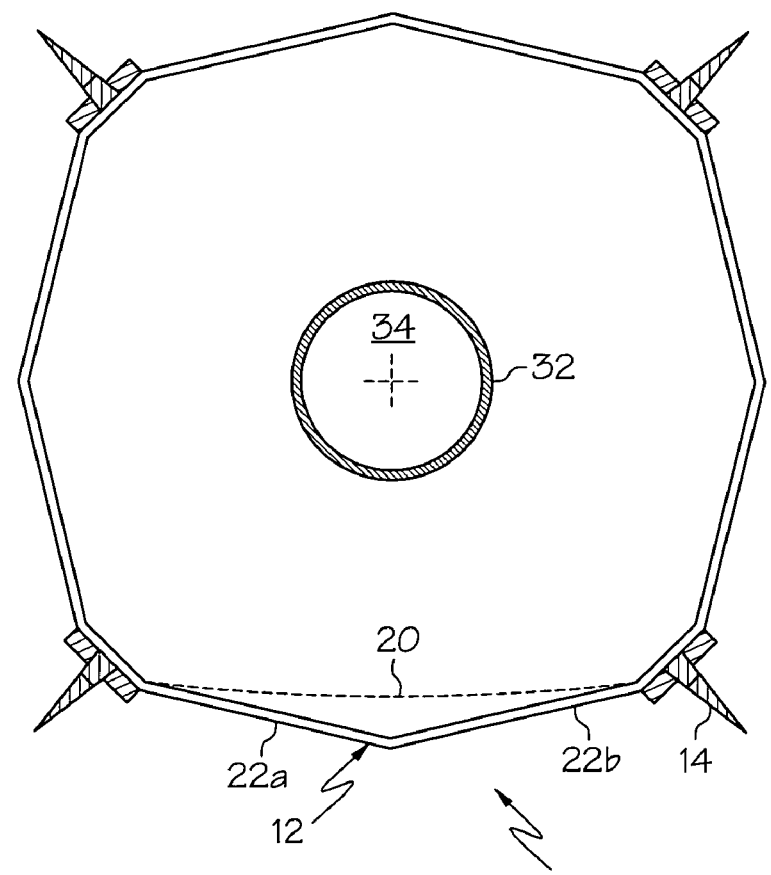
FIG. 5 is an expanded cross-sectional view of a cutting balloon similar to that shown in FIGS. 3 and 4 in an expanded state.

FIG. 5 illustrates generally at 10, a cross-sectional view of a similar dilatation balloon structure to that shown in FIG. 1 with the balloon in its fully expanded state.

Figure 6:
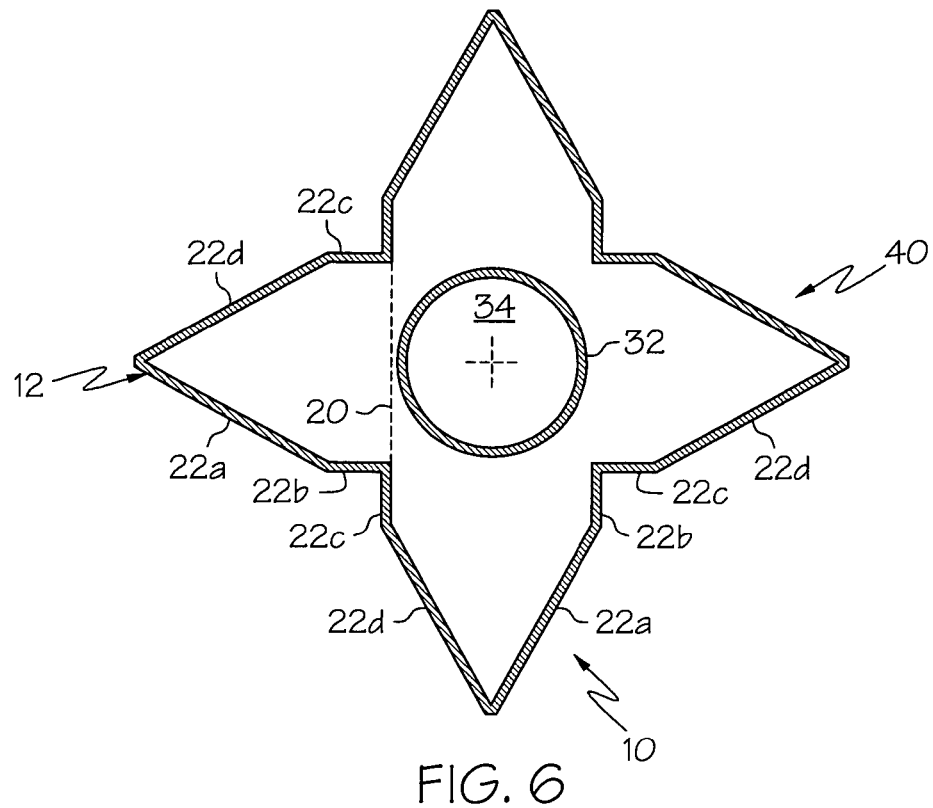
FIG. 6 is an expanded cross-sectional view of another embodiment of a dilatation balloon according to the invention in a deflated state.

FIG. 6 illustrates generally at 10, another embodiment of a balloon in a static state 40 having a substantially polygonal geometric structure according to the invention. In this embodiment, balloon 10 is shown with a four-wing structure, each wing having a substantially polygonal geometric shape which has five sides, i.e. a substantially pentagonal, in which the base is substantially straight, or may have a slight curvature. As can be each pentagon has four sides 22a, 22b, 22c, 22d wherein 22c, 22d are connected at base region 20. The resultant balloon thus has a structure wherein each wing 12 has a pentagonal geometric structure.

Figure 7:
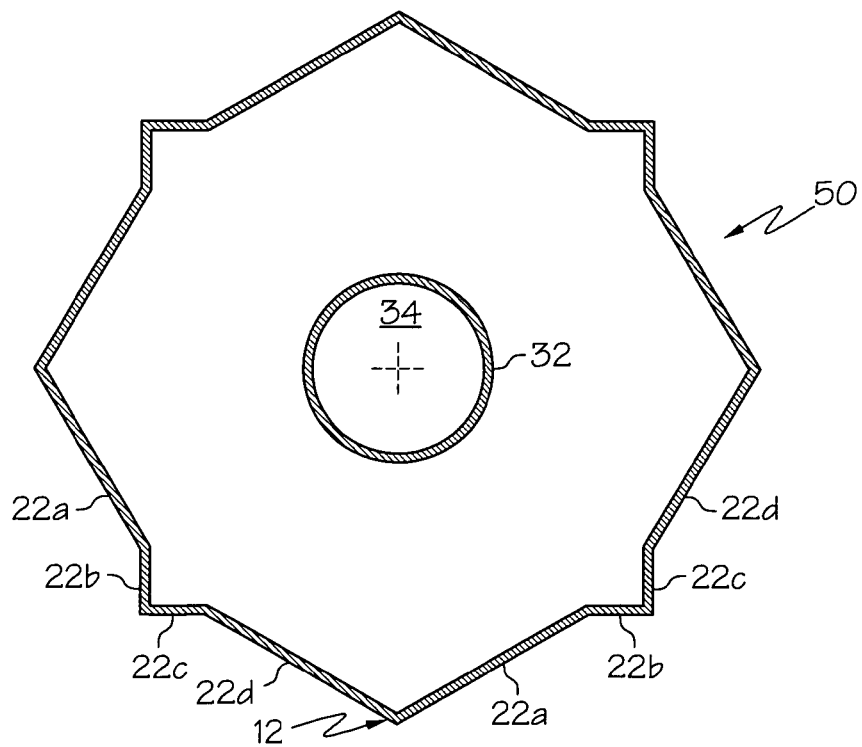
FIG. 7 is an expanded cross-sectional view of a balloon similar to that shown in FIG. 6 in an expanded state.
Figure 8:
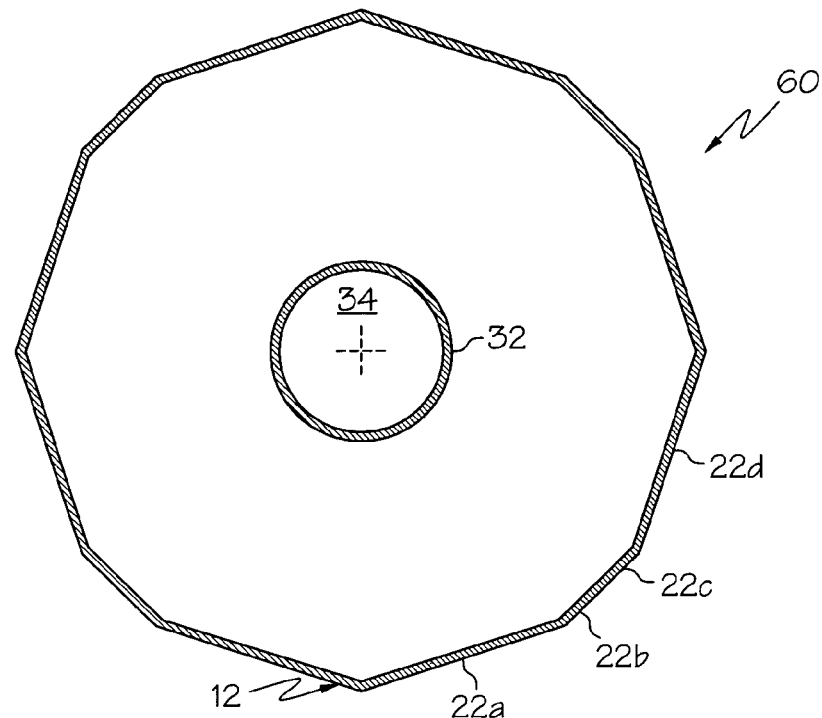
FIG. 8 is an expanded cross-sectional view of a balloon as in FIGS. 6 and 7 in a more highly expanded state.

FIG. 7 illustrates a balloon structure, which is substantially similar to that of FIG. 6 in one expanded state 50 and FIG. 8 is substantially the same balloon structure as that shown in FIG. 6 in an even more highly expanded state 60.

Figure 9:
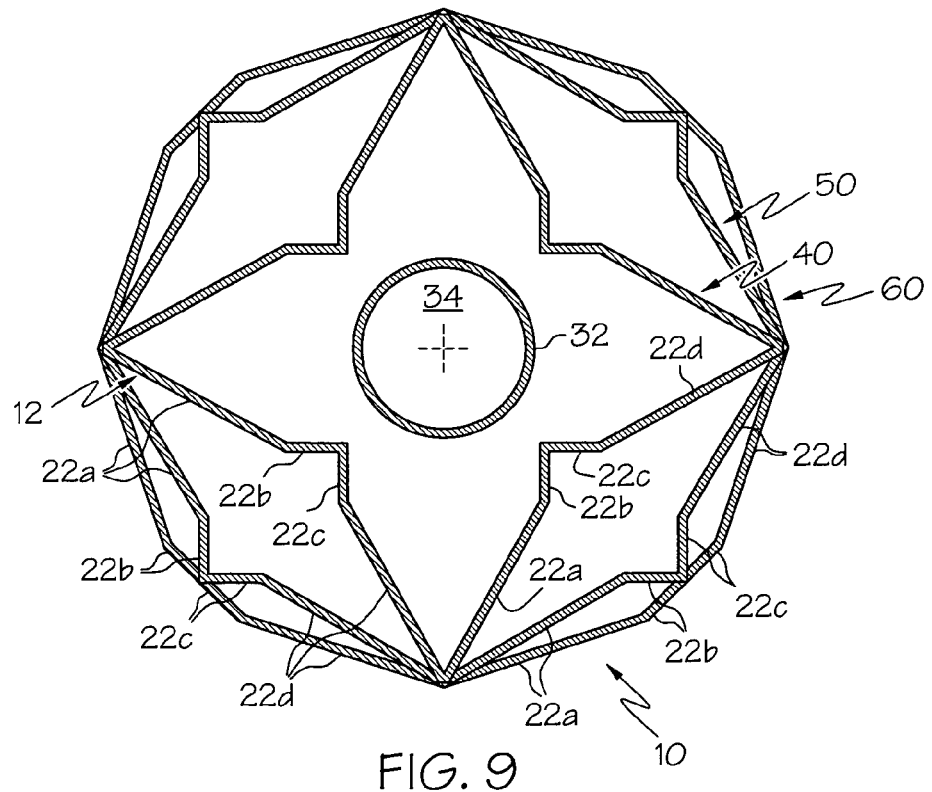
FIG. 9 shows the balloons of FIGS. 6-8.

FIG. 9 illustrates the balloon of FIGS. 6-8 in a static state 40 as shown in FIG. 6 and in a first expanded state 50 as shown in FIG. 7 and in a fully expanded state 60 as shown in FIG. 8.

Any suitable balloon forming techniques may be employed. Such techniques are known in the art. An example of one method is described in U.S. Pat. No. 4,490,421 to Levy which is incorporated by reference herein in its entirety.

The methods typically include the basic steps of extruding a tubular parison, placing the tubular parison in a balloon mold, and expanding the tubular parison into the desired balloon configuration in the balloon mold.

Desirably, the balloon is formed in a single molding step in which the configuration shown in FIG. 6, is the molded configuration.

Alternatively, the balloons according to the invention may be formed using a method which includes several molding steps wherein each configuration shown in FIGS. 6, 7 and 8 may be formed during a single molding step. For example, using one process, the second expanded configuration shown in FIG. 8 may be molded in a first mold during a first molding step, the first expanded configuration shown in FIG. 7 may be formed in a second mold during a second molding step, and the configuration of the balloon in its static state, shown in FIG. 6 may be formed in a third mold during a third molding step. While it is desirable to mold the most expanded configuration first, the order of such molding steps may be altered depending on the balloon configuration in each state. The balloon may have a first molded configuration corresponding to a second expanded state, a second molded configuration corresponding to a first expanded state, and a third molded configuration corresponding to a static state. The substantially polygonal geometric shape of the balloon in the first and second expanded states may be the same substantially polygonal geometric shape, or they may be different, and one or both may have a substantially polygonal geometric shape that is different from the substantially polygonal geometric shape of the third molded configuration, i.e. that exhibited in the static state. Of course, in the event that the balloon exhibits the same substantially polygonal geometric shape in both a first and second expanded state, only a two molding step process may be required. Each molding step may be followed by a heat set.

Any of the embodiments described herein may be molded in this fashion. Such a process is intended for illustrative purposes only, and not as a limitation on the scope of the invention. One of ordinary skill in the art would understand that the steps be altered depending on the balloon configurations desirable. Such a process employing more than one molding step is described in commonly assigned copending U.S. patent application Ser. No. 10/271,830, the entire content of which is incorporated by reference herein.

Figure 10:
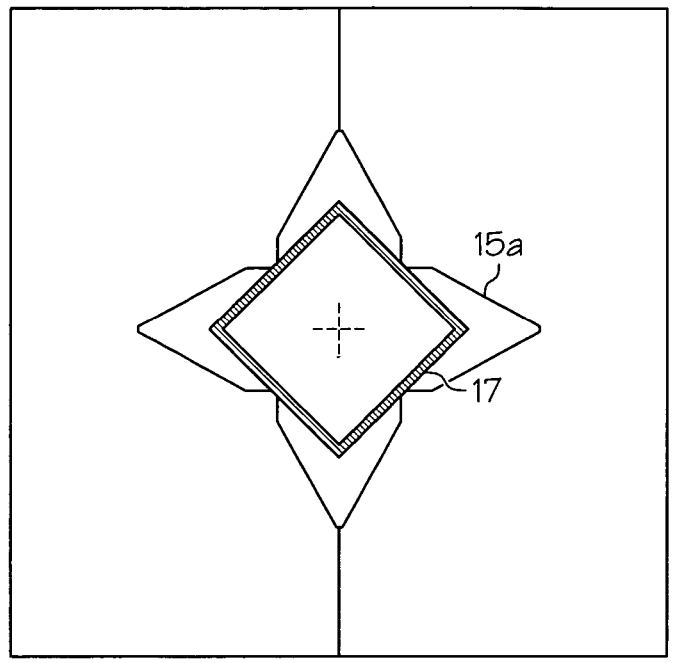
FIG. 10 is an expanded cross-sectional view of a geometric balloon mold having a four-point star structure shown with square tubing.

Using the method of the present invention may involve extruding the tubular parison into a substantially polygonal geometric shape, using a mold during balloon molding which has a substantially polygonal geometric shape, or both. For example, FIG. 10 illustrates a geometric balloon mold 15*a*, which may be employed for the formation of structures similar to that described in FIGS. 5 and 6, with square extruded tubing 17. Extrusion of such a polygonally shaped tubular parison may be accomplished by changing the shape of the extrusion die being employed. Inner and outer diameters may be extruded to have a different geometry. The balloon is considered to be in its "static state" when it comes out of the mold.

Figure 11:
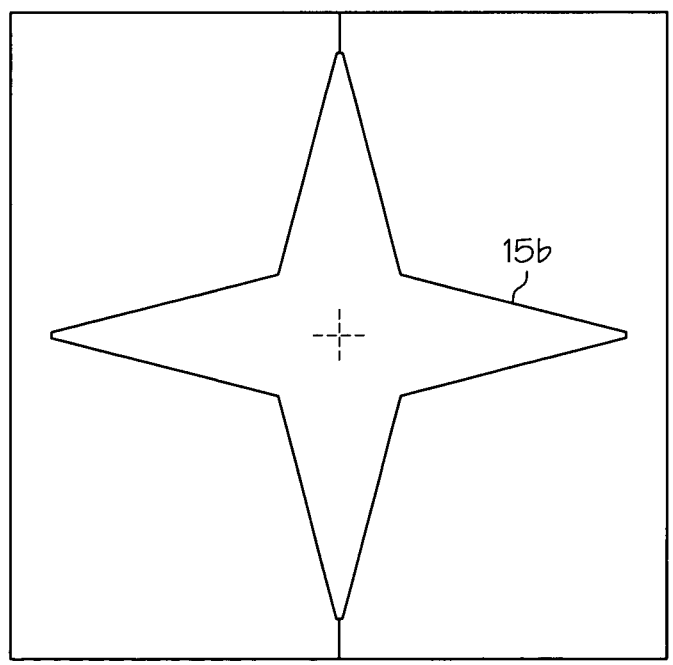
FIG. 11 is an expanded cross-sectional view of an alternative geometric four-point star balloon mold.

FIG. 11 illustrates an alternative balloon mold 15*b*, cross-sectional view, which may be employed in the formation of balloons similar to those shown in FIGS. 1-4.

Optionally, the balloon may be radially stretched or oriented when it is in the balloon mold, although this step may be conducted at other stages in the process as well. Stretching will typically either be conducted prior to balloon molding, i.e. when it is in a preform state, or during balloon molding. Optionally, the balloon may be post-mold heat set, although using the present method does not require heat setting.

The balloon is typically taken out of the mold in its static state. The balloon is then pressurized and the tubing ends are sealed. If atherotomes or blades are added, it may be accomplished at this point. The blades can be secured to the balloon using any method known in the art such as through bonding techniques. The balloon may then be disposed about the catheter shaft.

In any of the embodiments above, the balloon may be deflated from its static state, and the wings folded or wrapped around the catheter shaft. Typically, the balloon is partially reinflated prior to folding or wrapping.

In each of the embodiments described above, the vertices of the substantially polygonal geometric shape of the balloon may provide a guide along which the balloon may fold.

In a typical folding procedure, the balloon may be placed in a folding apparatus, negative pressure applied, and the balloon manipulated with impinging members or blades from the folding apparatus into its folded state.

After folding and wrapping of the balloon, a balloon protector may be added and the resultant assembly may then be sterilized.

Using the present method, after folding, no heat set of the balloon is required, although that is not to say that, a heat set cannot be used.

The balloon may be delivered through the vasculature of a patient to the site of use and expanded using inflation fluid. When inflation fluid is applied to the folded balloon, it causes the flaps to unwrap so that the balloon can inflate to its full inflated state. After use, the balloon is then evacuated, deflated, and removed from the vasculature. As stated above, the vertices of the substantially polygonal geometric shape of the balloon provide a guide along which the balloon refolds upon itself.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. An expandable balloon for a medical device having a static state, at least one first expanded state and at least one second expanded state, and said balloon having a longitudinal axis, said balloon having a substantially polygonal geometric shape in a cross-sectional view perpendicular to said longitudinal axis in said static state, and in said at least one first expanded state at a pressure of at least about 8 atmospheres.

2. The expandable balloon of claim 1, said balloon having a substantially polygonal geometric shape in said second expanded state.

3. The expandable balloon of claim 2, said substantially polygonal geometric shape of said balloon in said second expanded state is different than said substantially polygonal geometric shape of said balloon is said first expanded state.

4. The expandable balloon of claim 2 wherein said balloon in said second expanded state has eight or more sides.

5. The expandable balloon of claim 1 comprising a plurality of wings in said static state.

6. The expandable balloon of claim 5 wherein each of said plurality of wings has a substantially polygonal geometric shape.

7. The expandable balloon of claim 5 wherein each of said wings are equally spaced about a reference circle.

8. The expandable balloon of claim 1, said expandable balloon having a star-like structure, said star-like structure having four or more wings.

9. The expandable balloon of claim 8 wherein each wing has a substantially polygonal geometric shape, each wing having three or more sides.

10. The expandable balloon of claim 1, said substantially polygonal geometric shape of said balloon in said static state is different than said substantially polygonal geometric shape in said at least one first expanded state.

11. The expandable balloon of claim 1 further comprising atherotomes.

12. An expandable balloon for a medical device having at least one static state, at least one first expanded state and at least one second expanded state, said balloon comprising a plurality of wings in said static state, each wing having a substantially polygonal geometric shape in said static state and in said at least one first expanded state at a pressure of at least about 8 atmospheres.

13. A balloon catheter for dilating or recanalizing a vessel, said balloon catheter comprising an expandable balloon having a static state, at least one expanded state and at least one deflated state, said balloon having a longitudinal axis and wherein in a cross-sectional view perpendicular to said longitudinal axis, said balloon has a substantially polygonal geometric shape in said static state and in said at least one first expanded state at a pressure of at least about 8 atmospheres, said balloon further comprising atherotomes.

14. An expandable balloon for a medical device, the balloon having a first molded configuration, a second molded configuration and a third molded configuration, the balloon further having a longitudinal axis, and wherein in each configuration the balloon has a substantially polygonal geometric shape in a cross-sectional view which is perpendicular to the longitudinal axis, the first molded configuration corresponding to a static state, the second molded configuration corresponding to a first expanded state, and the third molded configuration corresponding to a second expanded state, wherein the first expanded state corresponds to an inflation pressure of at least about 8 atmospheres.

15. The balloon of claim 14 wherein said substantially polygonal geometric shape of said balloon in the second molded configuration, the third molded configuration or both, being different than the substantially polygonal geometric shape of said balloon in said first molded configuration.

16. An expandable balloon for a medical device, the balloon comprising atherotomes, and the balloon having a static state, at least one first expanded state and at least one second expanded state, the balloon further having a longitudinal axis, and wherein in a cross-sectional view perpendicular to said longitudinal axis, said balloon has a substantially polygonal geometric shape in said static state and in said at least one first expanded state, the at least one first expanded state occurs at an inflation pressure of at least about 8 atmospheres, the substantially polygonal geometric shape having three or more sides.

* * * * *